US010327892B2

(12) United States Patent
O'Connor et al.

(10) Patent No.: US 10,327,892 B2
(45) Date of Patent: Jun. 25, 2019

(54) INTEGRATED ADAPTIVE SEAL FOR PROSTHETIC HEART VALVES

(71) Applicant: BOSTON SCIENTIFIC SCIMED INC., Maple Grove, MN (US)

(72) Inventors: Tim O'Connor, Galway (IE); Pat O'Toole, Galway (IE); Patricia Kelly, Galway (IE); Coley Smyth, Co Clare (IE)

(73) Assignee: BOSTON SCIENTIFIC SCIMED INC., Maple Grove, MN (US)

( * ) Notice: Subject to any disclaimer, the term of this patent is extended or adjusted under 35 U.S.C. 154(b) by 112 days.

(21) Appl. No.: 15/219,526

(22) Filed: Jul. 26, 2016

(65) Prior Publication Data

US 2017/0042668 A1   Feb. 16, 2017

Related U.S. Application Data

(60) Provisional application No. 62/203,717, filed on Aug. 11, 2015.

(51) Int. Cl.
*A61F 2/24* (2006.01)
*B05D 1/02* (2006.01)
*B05D 1/18* (2006.01)
*B05D 3/00* (2006.01)

(52) U.S. Cl.
CPC .......... *A61F 2/2409* (2013.01); *A61F 2/2415* (2013.01); *A61F 2/2418* (2013.01); *B05D 1/02* (2013.01); *B05D 1/18* (2013.01); *B05D 3/007* (2013.01); *A61F 2210/0076* (2013.01); *A61F 2220/0025* (2013.01); *A61F 2250/0069* (2013.01)

(58) Field of Classification Search
CPC .... A61F 2/2409; A61F 2/2415; A61F 2/2418; B05D 1/02; B05D 1/18; B05D 3/007
See application file for complete search history.

(56) References Cited

U.S. PATENT DOCUMENTS

| 3,503,079 A | 3/1970 | Smith |
| 3,546,711 A | 12/1970 | Boyros |
| 3,551,913 A | 1/1971 | Shiley et al. |

(Continued)

FOREIGN PATENT DOCUMENTS

| EP | 2119417 A2 | 11/2009 |
| JP | 2006333940 A * | 12/2006 |

(Continued)

OTHER PUBLICATIONS

International Search Report and Written Opinion, PCT/US2016/045323, dated Feb. 2, 2017.

*Primary Examiner* — Andrew J Bowman
(74) *Attorney, Agent, or Firm* — Seager, Tufte & Wickhem LLP

(57) ABSTRACT

A support structure for a heart valve implant may include an expandable metallic scaffold configured to be actuated between a delivery configuration and a deployed configuration, and a seal member formed from a polymeric material, the seal member being disposed about the expandable scaffold, wherein a first portion of the seal member immediately adjacent the expandable scaffold is directly attached to the expandable scaffold and a second portion of the seal member immediately adjacent the expandable scaffold is unattached to the expandable scaffold.

8 Claims, 17 Drawing Sheets

(56) References Cited

U.S. PATENT DOCUMENTS

| | | |
|---|---|---|
| 3,570,014 A | 3/1971 | Hancock |
| 3,755,823 A | 9/1973 | Hancock |
| 3,983,581 A | 10/1976 | Angell et al. |
| 4,035,849 A | 7/1977 | Angell et al. |
| 4,340,977 A | 7/1982 | Brownlee et al. |
| 4,473,423 A | 9/1984 | Kolff |
| 4,484,365 A | 11/1984 | Murguet et al. |
| 4,490,859 A | 1/1985 | Black et al. |
| 4,510,628 A | 4/1985 | Kolff |
| 4,739,759 A | 4/1988 | Rexroth et al. |
| 5,258,023 A | 11/1993 | Reger |
| 5,326,372 A | 7/1994 | Mhatre et al. |
| 5,469,868 A | 11/1995 | Reger |
| 6,045,576 A | 4/2000 | Starr et al. |
| 6,254,636 B1 | 7/2001 | Peredo |
| 6,558,417 B2 | 5/2003 | Peredo |
| 6,719,789 B2 | 4/2004 | Cox |
| 6,883,522 B2 | 4/2005 | Spence et al. |
| 6,951,573 B1 | 10/2005 | Dilling |
| 7,172,625 B2 | 2/2007 | Shu et al. |
| 7,175,659 B2 | 2/2007 | Hill et al. |
| 7,261,732 B2 | 8/2007 | Justino |
| 7,318,278 B2 | 1/2008 | Zhang et al. |
| 7,329,279 B2 | 2/2008 | Haug et al. |
| 7,381,219 B2 | 6/2008 | Salahieh et al. |
| 7,445,631 B2 | 11/2008 | Salahieh et al. |
| 7,524,331 B2 | 4/2009 | Birdsall |
| 7,575,594 B2 | 8/2009 | Sieracki |
| 7,670,370 B2 | 3/2010 | Hill et al. |
| 7,717,955 B2 | 5/2010 | Lane et al. |
| 7,748,389 B2 | 7/2010 | Salahieh et al. |
| 7,780,725 B2 | 8/2010 | Haug et al. |
| 7,819,915 B2 | 10/2010 | Stobie et al. |
| 7,824,442 B2 | 11/2010 | Salahieh et al. |
| 7,824,443 B2 | 11/2010 | Salahieh et al. |
| 7,892,281 B2 | 2/2011 | Seguin et al. |
| 7,959,666 B2 | 6/2011 | Salahieh et al. |
| 7,959,672 B2 | 6/2011 | Salahieh et al. |
| 7,988,724 B2 | 8/2011 | Salahieh et al. |
| 7,993,394 B2 | 8/2011 | Hariton et al. |
| 8,012,135 B2 | 9/2011 | Dann et al. |
| 8,029,564 B2 | 10/2011 | Johnson et al. |
| 8,048,153 B2 | 11/2011 | Salahieh et al. |
| 8,052,749 B2 | 11/2011 | Salahieh et al. |
| 8,075,611 B2 | 12/2011 | Milwee et al. |
| 8,136,659 B2 | 3/2012 | Salahieh et al. |
| 8,163,014 B2 | 4/2012 | Lane et al. |
| 8,172,892 B2 | 5/2012 | Chuter et al. |
| 8,182,528 B2 | 5/2012 | Salahieh et al. |
| 8,226,710 B2 | 7/2012 | Nguyen et al. |
| 8,231,670 B2 | 7/2012 | Salahieh et al. |
| 8,246,678 B2 | 8/2012 | Salahieh et al. |
| 8,252,052 B2 | 8/2012 | Salahieh et al. |
| 8,992,608 B2 | 3/2015 | Haug et al. |
| 2002/0058994 A1 | 5/2002 | Hill et al. |
| 2002/0077698 A1 | 6/2002 | Peredo |
| 2003/0114924 A1 | 6/2003 | Moe |
| 2004/0015232 A1 | 1/2004 | Shu et al. |
| 2004/0030381 A1 | 2/2004 | Shu |
| 2004/0106990 A1 | 6/2004 | Spence et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0143809 A1 | 6/2005 | Salahieh et al. |
| 2005/0283231 A1 | 12/2005 | Haug et al. |
| 2006/0025854 A1 | 2/2006 | Lashinski et al. |
| 2006/0025855 A1 | 2/2006 | Lashinski et al. |
| 2006/0195184 A1 | 8/2006 | Lane et al. |
| 2006/0195185 A1 | 8/2006 | Lane et al. |
| 2006/0253191 A1 | 11/2006 | Salahieh et al. |
| 2006/0259137 A1 | 11/2006 | Artof et al. |
| 2006/0271172 A1 | 11/2006 | Tehrani |
| 2006/0287717 A1 | 12/2006 | Rowe et al. |
| 2007/0010876 A1 | 1/2007 | Salahieh et al. |
| 2007/0010877 A1 | 1/2007 | Salahieh et al. |
| 2007/0018214 A1 | 1/2007 | Ahn et al. |
| 2007/0027535 A1 | 2/2007 | Purdy, Jr. et al. |
| 2007/0129795 A1 | 6/2007 | Hill et al. |
| 2007/0162107 A1 | 7/2007 | Haug et al. |
| 2007/0203503 A1 | 8/2007 | Salahieh et al. |
| 2007/0244552 A1 | 10/2007 | Salahieh et al. |
| 2007/0282436 A1 | 12/2007 | Pinchuk |
| 2008/0033543 A1 | 2/2008 | Gurskis et al. |
| 2008/0125859 A1 | 5/2008 | Salahieh et al. |
| 2008/0234814 A1 | 9/2008 | Salahieh et al. |
| 2009/0240320 A1 | 9/2009 | Tuval et al. |
| 2010/0036484 A1 | 2/2010 | Hariton et al. |
| 2010/0082094 A1 | 4/2010 | Quadri et al. |
| 2010/0100176 A1 | 4/2010 | Elizondo et al. |
| 2010/0121434 A1 | 5/2010 | Paul et al. |
| 2010/0131054 A1 | 5/2010 | Tuval et al. |
| 2010/0137979 A1 | 6/2010 | Tuval et al. |
| 2010/0168844 A1 | 7/2010 | Toomes et al. |
| 2010/0191327 A1 | 7/2010 | Lane et al. |
| 2010/0249894 A1 | 9/2010 | Oba et al. |
| 2010/0249908 A1 | 9/2010 | Chau et al. |
| 2010/0249915 A1 | 9/2010 | Zhang |
| 2010/0249916 A1 | 9/2010 | Zhang |
| 2010/0249917 A1 | 9/2010 | Zhang |
| 2010/0249918 A1 | 9/2010 | Zhang |
| 2010/0256752 A1 | 10/2010 | Forster et al. |
| 2010/0262231 A1 | 10/2010 | Tuval et al. |
| 2010/0280495 A1 | 11/2010 | Paul et al. |
| 2011/0000073 A1 | 1/2011 | O'Fallon et al. |
| 2011/0098802 A1 | 4/2011 | Braido et al. |
| 2011/0125258 A1 | 5/2011 | Centola |
| 2011/0166648 A1 | 7/2011 | Robin et al. |
| 2011/0172765 A1 | 7/2011 | Nguyen et al. |
| 2011/0213460 A1 | 9/2011 | Lashinski et al. |
| 2011/0218619 A1 | 9/2011 | Benichou et al. |
| 2011/0224781 A1 | 9/2011 | White |
| 2011/0230956 A1 | 9/2011 | White |
| 2011/0245918 A1 | 10/2011 | White |
| 2011/0257735 A1 | 10/2011 | Salahieh et al. |
| 2011/0276128 A1 | 11/2011 | Cao et al. |
| 2011/0276129 A1 | 11/2011 | Salahieh et al. |
| 2011/0319991 A1 | 12/2011 | Hariton et al. |
| 2012/0016469 A1 | 1/2012 | Salahieh et al. |
| 2012/0016471 A1 | 1/2012 | Salahieh et al. |
| 2012/0022629 A1 | 1/2012 | Perera et al. |
| 2012/0029627 A1 | 2/2012 | Salahieh et al. |
| 2012/0041549 A1 | 2/2012 | Salahieh et al. |
| 2012/0041550 A1 | 2/2012 | Salahieh et al. |
| 2012/0053683 A1 | 3/2012 | Salahieh et al. |
| 2012/0059454 A1 | 3/2012 | Milwee et al. |
| 2012/0078356 A1 | 3/2012 | Fish et al. |
| 2012/0078357 A1 | 3/2012 | Conkin |
| 2012/0089224 A1 | 4/2012 | Haug et al. |
| 2012/0095549 A1 | 4/2012 | Forster et al. |
| 2012/0101567 A1* | 4/2012 | Jansen ................ A61F 2/2418 623/1.16 |
| 2012/0136432 A1 | 5/2012 | Forster et al. |
| 2012/0143316 A1 | 6/2012 | Seguin et al. |
| 2012/0185039 A1 | 7/2012 | Tuval et al. |
| 2012/0226348 A1 | 9/2012 | Lane et al. |
| 2012/0232459 A1 | 9/2012 | Dann et al. |
| 2012/0245706 A1 | 9/2012 | Alavi et al. |
| 2012/0259409 A1 | 10/2012 | Nguyen et al. |
| 2013/0090729 A1 | 4/2013 | Gregg et al. |

(56) References Cited

U.S. PATENT DOCUMENTS

2014/0005772 A1\* 1/2014 Edelman ............... A61F 2/2412
                                                          623/2.17
2014/0172077 A1    6/2014 Bruchman et al.

FOREIGN PATENT DOCUMENTS

| WO | WO-0106958 A1 \* | 2/2001 | ........... A61F 2/2403 |
| WO | 2006127412 A1 | 11/2006 | |
| WO | 2013012801 A2 | 1/2013 | |
| WO | 2014008207 A1 | 1/2014 | |
| WO | 2016126511 A2 | 8/2016 | |

\* cited by examiner

INTEGRATED ADAPTIVE SEAL FOR PROSTHETIC HEART VALVES

RELATED APPLICATIONS

This application claims the benefits of U.S. Provisional Application No. 62/203,717, filed Aug. 11, 2015.

TECHNICAL FIELD

The present disclosure pertains to medical devices, and methods for manufacturing medical devices. More particularly, the present disclosure pertains to medical devices for a replacement heart valve and methods for manufacturing medical devices for a replacement heart valve.

BACKGROUND

A wide variety of intracorporeal medical devices have been developed for medical use, for example, intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

In a first aspect, a support structure for a heart valve implant may comprise an expandable metallic scaffold configured to be actuated between a delivery configuration and a deployed configuration, and a seal member formed from a polymeric material. The seal member may be disposed about the expandable scaffold, wherein a first portion of the seal member immediately adjacent the expandable scaffold is not directly attached to the expandable scaffold. A temporary masking may be disposed on the expandable scaffold where the second portion of the seal member is immediately adjacent the expandable scaffold.

In addition or alternatively, and in a second aspect, the seal member is formed by application of the polymeric material directly onto the expandable scaffold and the temporary masking disposed thereon, followed by subsequent removal of the masking such that the second portion of the seal member is unattached to the expandable scaffold.

In addition or alternatively, and in a third aspect, the polymeric material is applied directly onto the expandable scaffold and the masking in liquid form.

In addition or alternatively, and in a fourth aspect, the polymeric material is sprayed onto the expandable scaffold and the masking.

In addition or alternatively, and in a fifth aspect, the expandable scaffold and the masking are dipped into the polymeric material.

In addition or alternatively, and in a sixth aspect, the polymeric material is roll coated onto the expandable scaffold and the masking.

In addition or alternatively, and in a seventh aspect, the masking is removed after the polymeric material has cured.

In addition or alternatively, and in an eighth aspect, when the expandable scaffold is in the delivery configuration, the second portion of the seal member lies flush against an outer surface of the expandable scaffold.

In addition or alternatively, and in a ninth aspect, when the expandable scaffold is in the deployed configuration, the second portion of the seal member bulges radially outward from the expandable scaffold.

In addition or alternatively, and in a tenth aspect, the seal member includes a plurality of layers of the polymeric material.

In addition or alternatively, and in an eleventh aspect, the seal member includes a distal reinforcing band at least partially embedded within the polymeric material.

In addition or alternatively, and in a twelfth aspect, a method of making a support structure for a heart valve implant may comprise positioning an expandable metallic scaffold on a mandrel in a coating apparatus, the expandable scaffold having a seal portion configured to receive a polymeric material thereon, applying a masking to at least one section of the seal portion of the expandable scaffold, applying a first layer of the polymeric material onto the seal portion of the expandable scaffold to form a seal member, curing the first layer, applying a second layer of the polymeric material onto the first layer, curing the second layer, dissolving the masking off of the at least one section of the seal portion of the expandable scaffold, and removing the expandable scaffold from the mandrel.

In addition or alternatively, and in a thirteenth aspect, a method of making a support structure for a heart valve implant may further comprise applying a third layer of the polymeric material onto the second layer, and curing the third layer.

In addition or alternatively, and in a fourteenth aspect, before applying the third layer, a reinforcing band is positioned around the expandable scaffold at a distal end thereof. Applying the third layer at least partially embeds the reinforcing band within the polymeric material.

In addition or alternatively, and in a fifteenth aspect, the masking is water soluble.

In addition or alternatively, and in a sixteenth aspect, dissolving the masking includes applying water to the expandable scaffold.

In addition or alternatively, and in a seventeenth aspect, after dissolving the masking, the seal member is unattached to the expandable scaffold at the at least one section of the seal portion.

In addition or alternatively, and in an eighteenth aspect, a method of making a support structure for a heart valve implant may further include adding one or more reinforcing members to the polymeric material prior to curing.

In addition or alternatively, and in a nineteenth aspect, applying the layers of polymeric material includes spraying the polymeric material.

In addition or alternatively, and in a twentieth aspect, applying the layers of polymeric material include dipping the seal portion of the expandable scaffold into the polymeric material.

The above summary of some embodiments, aspects, and/or examples is not intended to describe each disclosed embodiment or every implementation of the present disclosure. The Figures, and Detailed Description, which follow, more particularly exemplify these embodiments.

Figure 1:
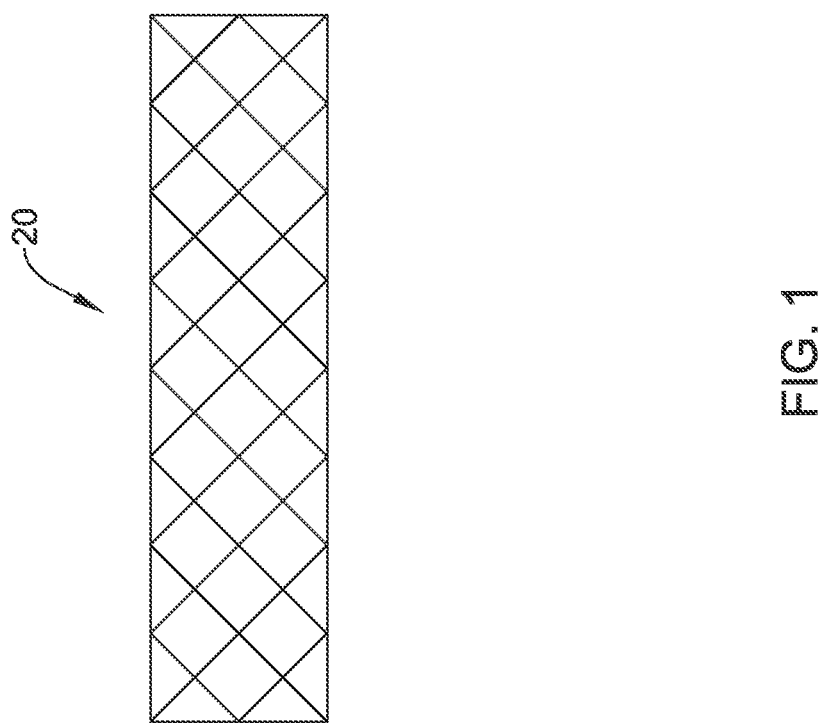
FIG. 1 illustrates an example expandable scaffold of an example support structure in a delivery configuration.

While the invention is amenable to various modifications and alternative forms, specifics thereof have been shown by way of example in the drawings and will be described in greater detail below. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. Other relative terms, such as "upstream" and "downstream" refer to a direction of fluid flow within a lumen, such as a body lumen or blood vessel.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact the cardiovascular system are prevalent in the United States and throughout the world. Traditionally, treatment of the cardiovascular system was often conducted by directly accessing the impacted part of the system. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed, for example, where a blocked coronary artery could be accessed and treated via a percutaneous catheter (e.g., angioplasty). Such therapies have gained wide acceptance among patients and clinicians.

Some relatively common medical conditions may include or be the result of inefficiency, ineffectiveness, or complete failure of one or more of the valves within the heart. For example, failure of the aortic valve can have a serious effect on a human and could lead to serious health condition and/or death if not dealt with. Treatment of defective heart valves poses other challenges in that the treatment often requires the repair or outright replacement of the defective valve. Such therapies may be highly invasive to the patient. Disclosed herein are medical devices and methods for making medical devices that may be used for delivering a medical device to a portion of the cardiovascular system in order to diagnose, treat, and/or repair the system. At least some of the medical devices disclosed herein may be used in the delivery and implantation of a replacement heart valve (e.g., a replacement aortic valve). In addition, the devices disclosed herein may deliver the replacement heart valve percutaneously and, thus, may be much less invasive to the patient. The devices disclosed herein may also provide a number of additional desirable features and benefits as described in more detail below.

In some embodiments, the disclosure generally pertains to an adaptive seal for a heart valve implant comprising a seal member disposed proximate a distal end of an expandable scaffold of a heart valve implant. The seal may serve to minimize or eliminate paravalvular regurgitation or leakage following implantation.

Figure 2:
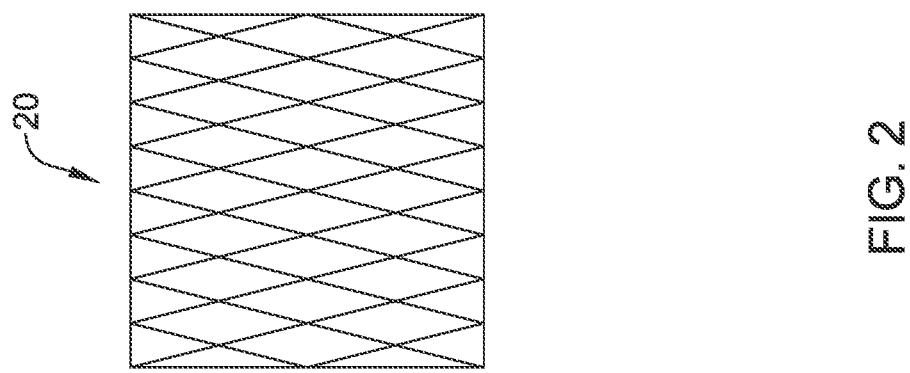
FIG. 2 illustrates an example expandable scaffold of an example support structure in a deployed configuration.

In some embodiments, a support structure 10 for a heart valve implant may include an expandable scaffold 20 configured to be actuated between a delivery configuration, illustrated schematically in FIG. 1 for example, and a deployed configuration, illustrated schematically in FIG. 2 for example. In general, the expandable scaffold 20 may take the form of a braid, a stent, a mesh, or other suitable arrangement. In some embodiments, the expandable scaffold 20 may form a generally tubular structure, a generally cylindrical structure, or other suitable structure. In addition, "generally cylindrical" is to be interpreted as encompassing transverse cross-sections which depart from strictly circular in an unconstrained condition. In some embodiments, the expandable scaffold 20 may define a central longitudinal axis extending axially through a central lumen of the expandable scaffold 20. In some embodiments, a heart valve implant may include a plurality of valve leaflets (not shown) disposed within the central lumen of the expandable scaffold 20.

In some embodiments, the expandable scaffold 20 may be formed from a metallic material, thus forming an expandable metallic scaffold. In some embodiments, the expandable scaffold 20 may be formed from a polymeric material, thus forming an expandable polymeric scaffold. Accordingly, the various terms "expandable scaffold", "expandable metallic scaffold", and "expandable polymeric scaffold" may be used interchangeably throughout the disclosure, wherein only a difference in material may be expressly defined by the different terms. As such, the more general term "expandable scaffold" may include either an expandable metallic scaffold or an expandable polymeric scaffold, or the term "expandable scaffold" may refer to both of an expandable metallic scaffold and an expandable polymeric scaffold.

Some suitable metallic materials for the expandable scaffold 20 may include, but are not necessarily limited to, stainless steel, tantalum, tungsten, nickel-titanium alloys such as those possessing shape memory properties commonly referred to as nitinol, nickel-chromium alloys, nickel-chromium-iron alloys, cobalt-chromium-nickel alloys, or other suitable metals, or combinations or alloys thereof.

Figure 14:
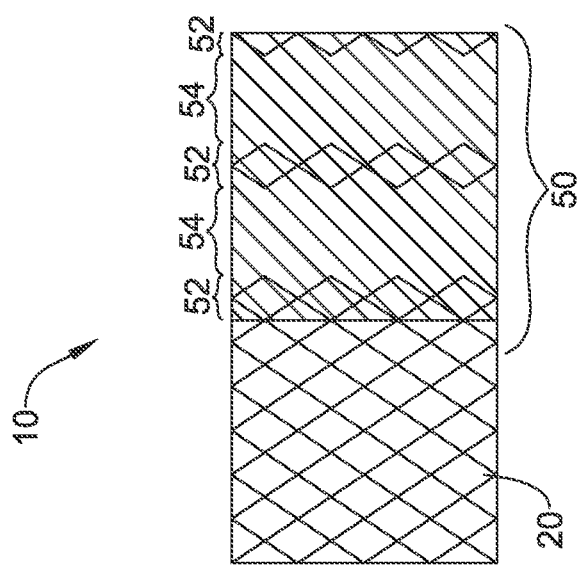
Figure 14A:
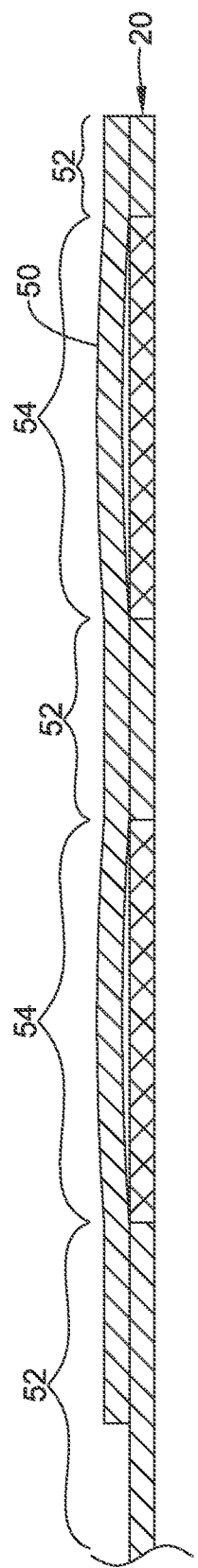
FIG. 14A is a partial cross-sectional view of an example support structure.

In some embodiments, a support structure 10 for a heart valve implant may include a seal member 50. In some embodiments, the seal member 50 may be disposed about the expandable scaffold 20 and/or coupled to the expandable scaffold 20. In some embodiments, a first portion 52 of the seal member 50 immediately adjacent the expandable scaffold 20 may be directly attached to the expandable scaffold 20. In some embodiments, a second portion 54 of the seal member 50 immediately adjacent the expandable scaffold 20 may not be directly attached to the expandable scaffold 20, as seen in FIG. 14A for example. In some embodiments, the seal member 50 may be formed from a polymeric material, as will be described in more detail below.

Figure 3:
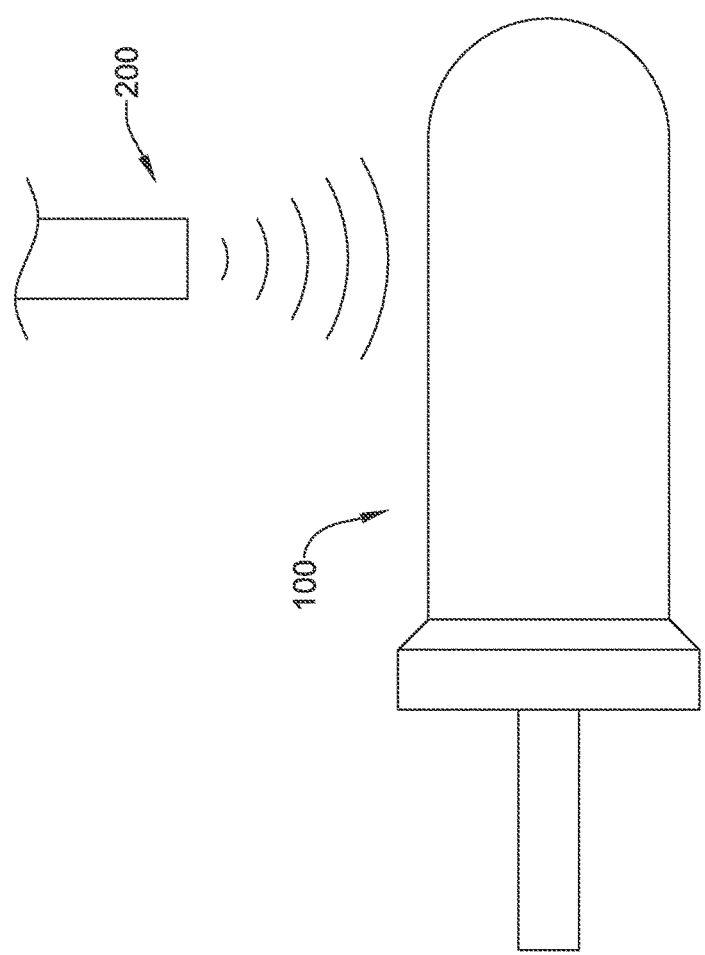
FIG. 3 illustrates an example mandrel usable in an example method of making a support structure.
Figure 4:
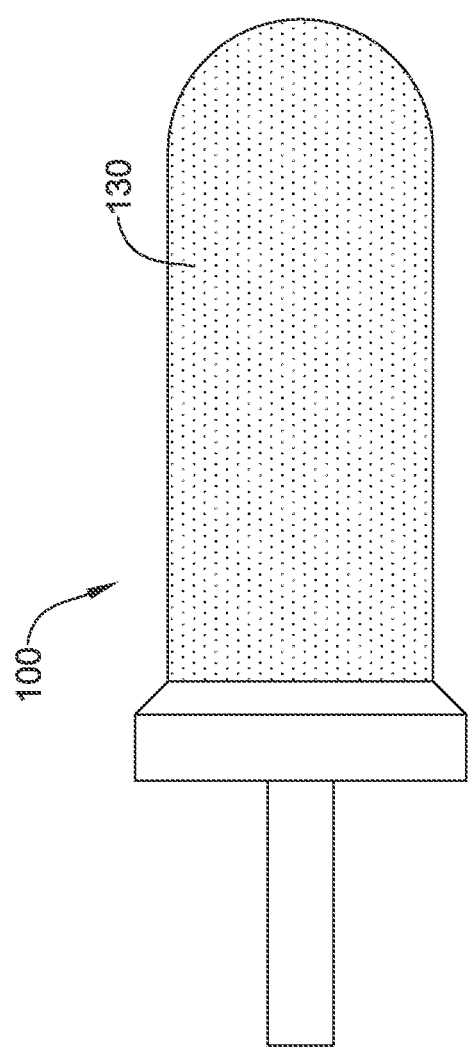
FIGS. 4-14 illustrate an example method of making an example support structure.

FIG. 3 illustrates an example mandrel 100 disposed adjacent a spraying apparatus 200 in an example coating apparatus. A coating apparatus, as it pertains to the instant disclosure, may include a number of suitable means of applying a polymeric material to the mandrel 100 and/or the expandable scaffold 20 disposed thereon. For example, some suitable, non-limiting examples of a coating apparatus may include a spraying apparatus 200, a dipping tank 210, and/or a roll-coating apparatus 220. Other types or examples of a coating apparatus may also be used. In at least some embodiments, the mandrel 100 may include a masking 130 applied thereto, as seen in FIG. 4 for example, which allows the support structure 10 to be removed from the mandrel 100 with relative ease upon completion of the fabrication process. For example, in some embodiments, the masking 130 may be dissolved to create a small space between the mandrel 100 and the support structure 10, and/or to break a bond formed therebetween as a result of curing the polymeric material applied thereto in the fabrication process, thereby allowing the support structure 10 to slip off of the mandrel 100. In some embodiments, an expandable scaffold 20 may be positioned on a mandrel 100 in a coating apparatus, the expandable scaffold 20 having a seal portion 22 configured to receive a polymeric material thereon, as seen in FIG. 5 for example.

Figure 5:
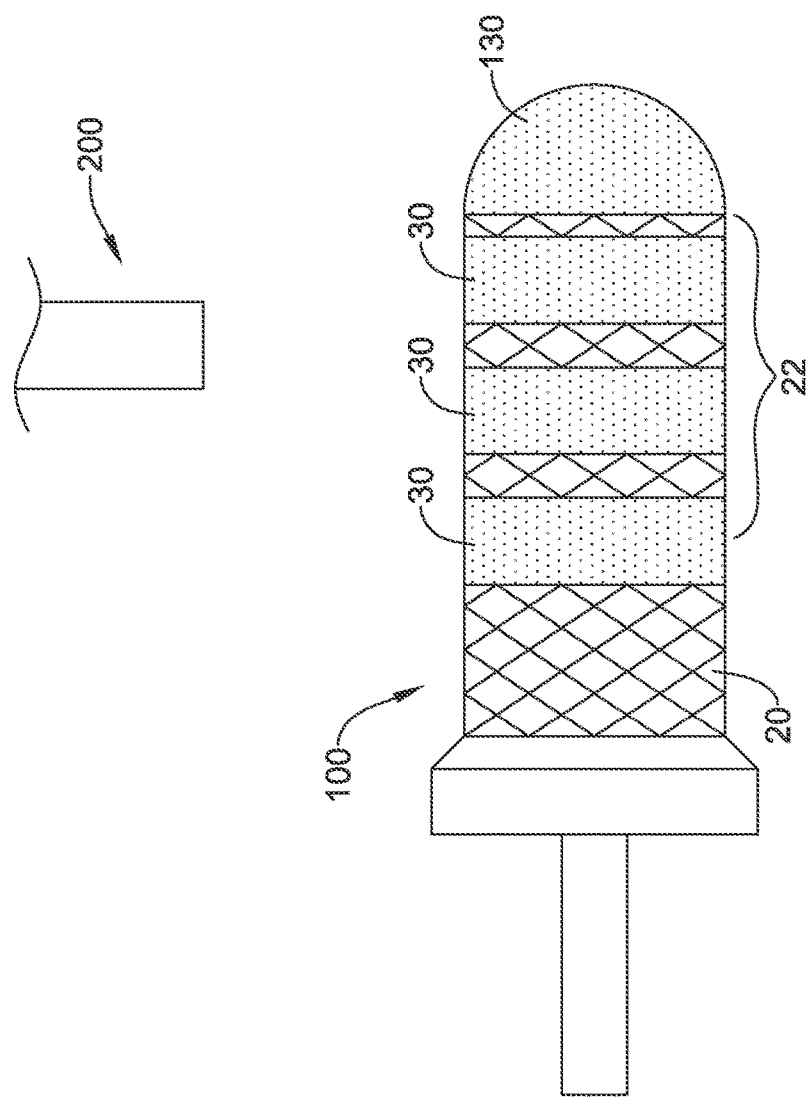
Figure 6:
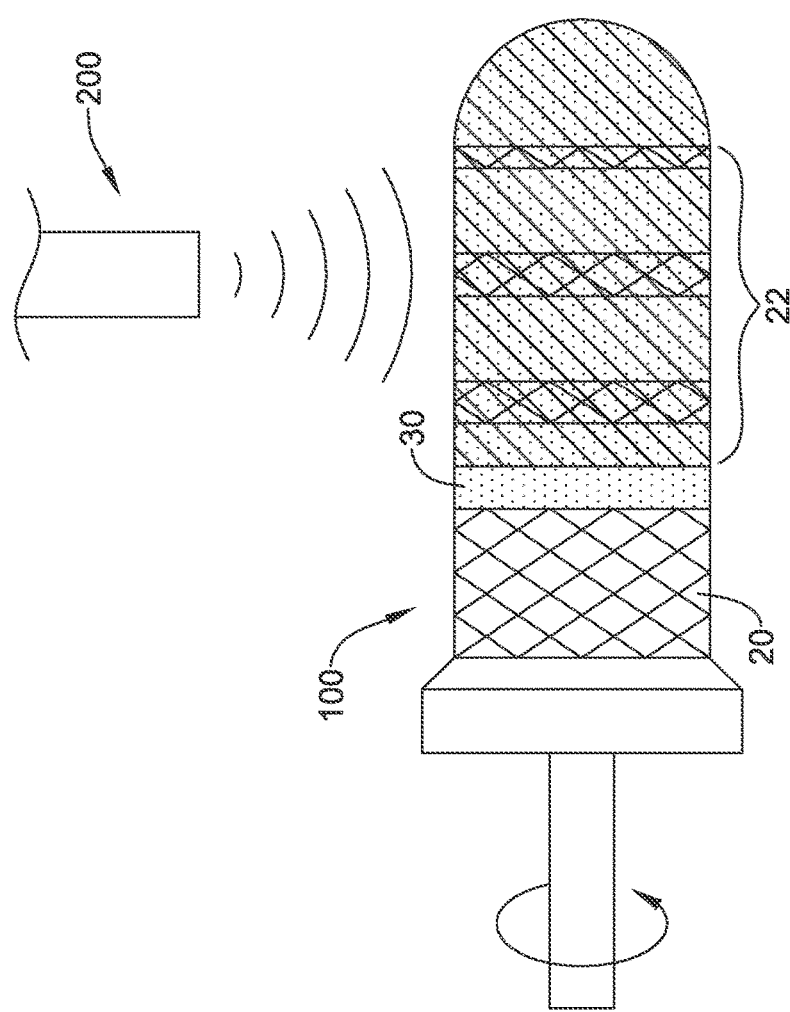
Figure 7:
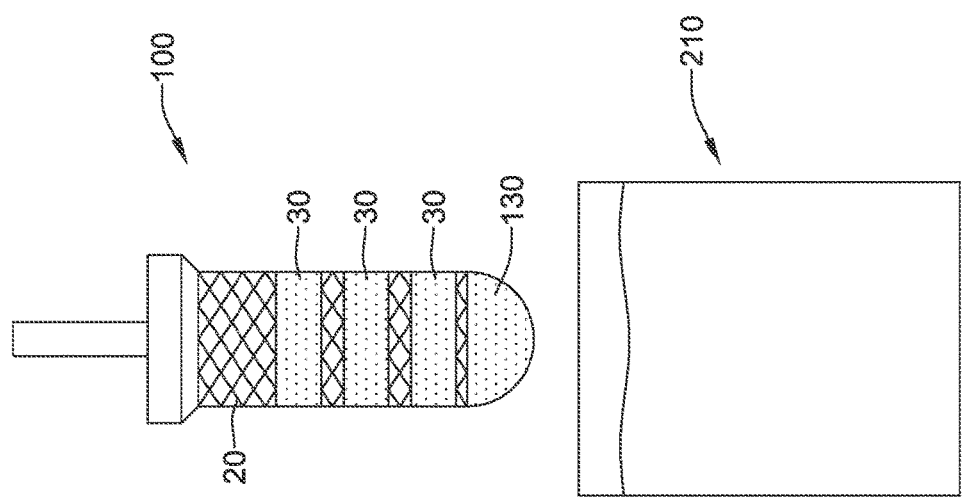
Figure 8:
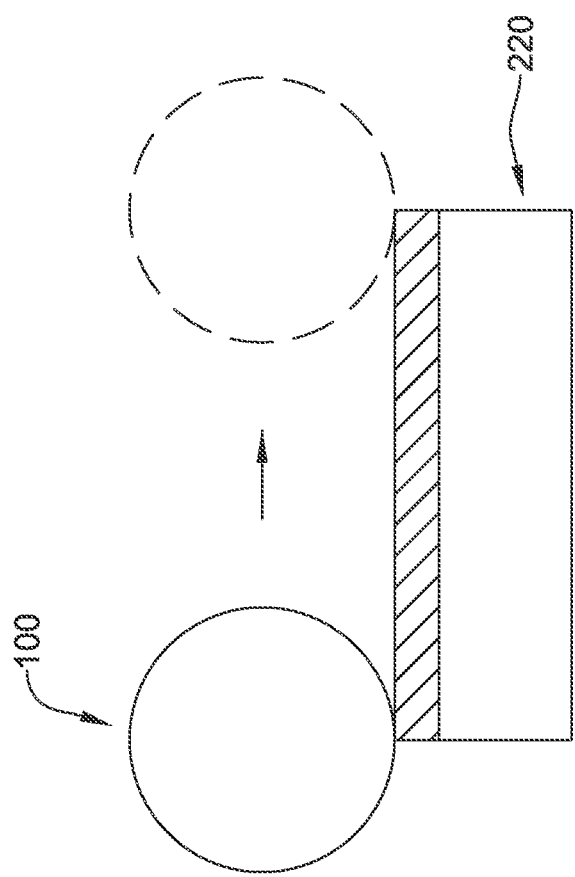

In some embodiments, a temporary masking 30 may be applied to at least one section of the seal portion 22 of the expandable scaffold 20, as seen in FIG. 5 for example. In some embodiments, the seal member 50 may be formed by application of the polymeric material directly onto the expandable scaffold 20 (i.e., the seal portion 22) and the temporary masking 30 disposed thereon where the second portion 54 of the seal member 50 is to be formed (i.e., the at least one section of the seal portion 22), followed by subsequent removal of the temporary masking 30 such that the second portion 54 of the seal member 50 is unattached to the expandable scaffold 20. In some embodiments, the polymeric material may be applied directly onto the expandable scaffold 20 and the temporary masking 30 in liquid form. In some embodiments, the polymeric material may be sprayed directly onto the expandable scaffold 20 and the temporary masking 30 by a spraying apparatus 200, as seen in FIG. 6 and described herein. In some embodiments, the mandrel 100 may be rotated about a longitudinal axis thereof while the spraying apparatus 200 applies the polymeric material to the expandable scaffold 20 and the temporary masking 30. In some embodiments, the expandable scaffold 20 and the temporary masking 30 may be dipped into the polymeric material, which may be disposed within a dipping tank 210 at a sufficient depth to receive a mandrel 100, as seen in FIG. 7 and described herein, having the expandable scaffold 20 disposed thereon. In some embodiments, the mandrel 100 may be rotated about a longitudinal axis thereof while the mandrel 100 the polymeric material is applied to the expandable scaffold 20 and the temporary masking 30. In some embodiments, the polymeric material may be roll coated onto the expandable scaffold 20 and the temporary masking 30, wherein the polymeric material may be disposed in or on a roll-coating apparatus 220 at a sufficient depth to coat the expandable scaffold 20 disposed on the mandrel 100, as seen in FIG. 8 and described herein.

FIG. 3 illustrates an example coating apparatus having an example mandrel 100 disposed adjacent a spraying apparatus 200. In at least some embodiments, the mandrel 100 may include a masking 130 applied thereto before an expandable scaffold 20 is positioned on the mandrel 100, as seen in FIG. 4 for example, which allows the support structure 10 to be removed from the mandrel 100 with relative ease upon completion of the fabrication process. For example, in some embodiments, after curing the polymeric material, the masking 130 may be dissolved to create a small space between the mandrel 100 and the support structure 10, and/or to break a bond formed therebetween as a result of curing the polymeric material applied thereto in the fabrication process, thereby allowing the support structure 10 to slip off of the mandrel 100.

In some embodiments, the mandrel 100 may include a taper. In other embodiments, the mandrel 100 may include two or more regions having different degrees of taper. In some embodiments, a mandrel 100 may include grooves. Such grooves may produce a transverse cross section which is fluted, undulated, and/or ribbed. Of course, various tapers and/or grooving may be combined in a single mandrel 100 if desired.

In some embodiments, the seal member 50 may include a plurality of layers of polymeric material. For example, in some embodiments, a radially innermost layer may comprise a polycarbonate and a polyurethane; a radially outermost layer may comprise a polycarbonate and a polyurethane; at least one inner layer disposed between the radially outermost layer and the radially innermost layer may comprise a polycarbonate and a polyurethane. These are only examples. Other suitable polymeric materials are also contemplated. Some suitable polymeric materials may include, but are not necessarily limited to, polyamide, polyether block amide, polyethylene, polyethylene terephthalate, polypropylene, polyvinylchloride, polytetrafluoroethylene, polysulfone, and copolymers, blends, mixtures or combinations thereof.

Figure 9:
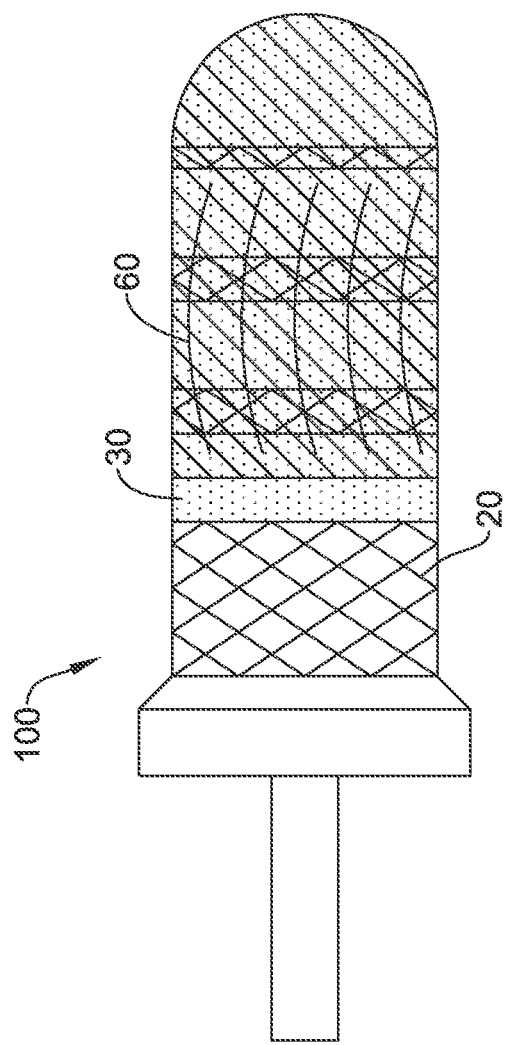

In some embodiments, the modulus of elasticity of the inner layer may be less than the modulus of elasticity of the radially innermost outer layer and/or the modulus of elasticity of the radially outermost outer layer. In other embodiments, the elongation to break of the inner layer may be greater than the elongation to break of the radially innermost outer layer and/or the elongation to break of the radially outermost outer layer. Although the radially innermost outer layer and the radially outermost outer layer may comprise the same material, it will be appreciated that they may be compositionally the same or different. In addition to the radially innermost outer layer, the at least one inner layer, and the radially outermost outer layer, the seal member 50 may also include a reinforcement, a reinforcing layer, and/or one or more reinforcing members 60 added to the polymeric material prior to curing, as seen in FIG. 9. The reinforcement, the reinforcing layer, and/or the one or more reinforcing members 60 may comprise a woven or nonwoven fabric and may be positioned within or between the various layers. In some embodiments, the reinforcement, the reinforcing layer, and/or the one or more reinforcing members 60 may be positioned on a radially innermost surface or radially outermost surface of the seal member 50. In some embodiments, the reinforcement, the reinforcing layer, and/or the one or more reinforcing members 60 may be generally aligned. In some embodiments, the reinforcement, the reinforcing layer, and/or the one or more reinforcing members 60 may be randomly oriented and/or disposed on the seal member 50. As noted elsewhere, the reinforcement, the reinforcing layer, the one or more reinforcing members 60, and/or the reinforcing band(s) 70 (described below) may include perforations. In some embodiments, the perforations may extend completely through the seal member 50.

Figure 10:
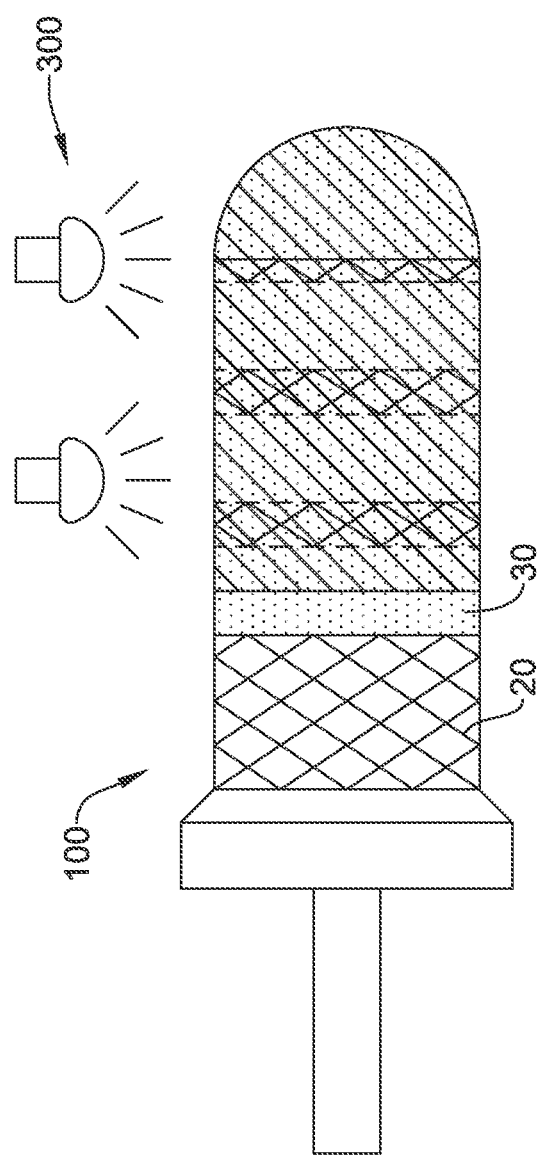

The seal member 50 may be formed in a variety of ways, for example it may be formed by successive applications of a polymeric material, such as for example a polymer solution, to a seal portion 22 of the expandable scaffold 20 positioned on an appropriately shaped mandrel 100, as illustrated in FIGS. 6-8. Following a careful cleaning of the mandrel 100, the mandrel 100 may be mounted to an appropriate holding fixture in a coating apparatus. An expandable scaffold 20 may be positioned on the mandrel 100 in the coating apparatus, the expandable scaffold 20 having a seal portion 22 configured to receive a polymeric material thereon. In some embodiments, a first layer of a polymeric material, such as a polymer solution comprising a carrier and at least one polymer, may be applied to the seal portion 22 of the expandable scaffold 20, and in some embodiments, subsequently cured or dried, such as with a curing apparatus 300, as seen in FIG. 10 for example. In some embodiments, the polymer solution may include a polycarbonate, a polyurethane, and/or a volatile carrier. The polymeric material and/or the polymer solution may be applied as a single layer or multiple layers to achieve the desired thickness of the seal member 50.

In some embodiments, a second layer of the polymeric material, such as the polymer solution comprising the carrier and the at least one polymer may be applied to the seal portion 22, and in some embodiments, subsequently cured or dried, such as with a curing apparatus 300, as seen in FIG. 10 for example. In some embodiments, the first layer may not necessarily be cured or dried prior to applying the second layer to the seal portion 22. In some embodiments, the polymer solution may include a polycarbonate, a polyurethane, and/or a volatile carrier. The second layer may be applied as a single layer or as multiple layers to achieve the desired thickness of the seal member 50. In some embodiments, the second layer may be different from the first layer. In other embodiments, the second layer may be the same as the first layer.

In some embodiments, a third layer of the polymeric material, such as the polymer solution comprising the carrier and the at least one polymer may be applied to the seal portion 22, and in some embodiments, subsequently cured or dried, such as with a curing apparatus 300, as seen in FIG. 10 for example. In some embodiments, the second layer may not necessarily be cured or dried prior to applying the third layer to the seal portion 22. In some embodiments, the third layer may include a polycarbonate, a polyurethane, and/or a volatile carrier. The third layer may be applied as a single layer or multiple layers to achieve the desired thickness of the seal member 50. In some embodiments, the third layer may be different from the first and/or the second layer. In other embodiments, the third layer may be the same as the first and/or the second layer.

Figure 11:
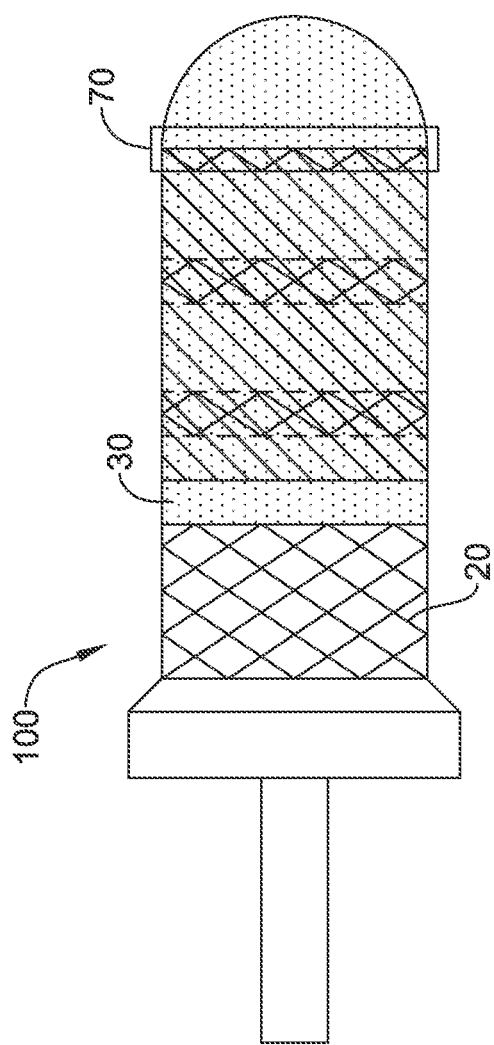
Figure 12:
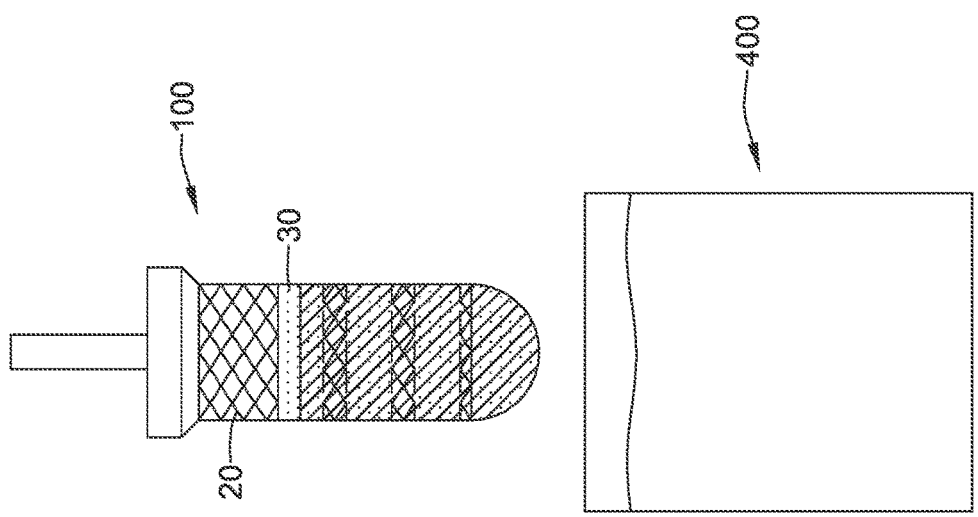

In some embodiments, the support structure 10 and/or the seal member 50 may include a distal reinforcing band 70, as seen for example in FIG. 11. In some embodiments, the support structure 10 and/or the seal member 50 may include a distal reinforcing band 70 attached to and/or coupled with the polymeric material of the seal member 50. In some embodiments, the support structure 10 and/or the seal member 50 may include a distal reinforcing band 70 at least partially embedded within the polymeric material of the seal member 50.

In some embodiments, the distal reinforcing band 70 may be formed from a woven or nonwoven fabric and either incorporated within the interior of the seal member 50 or adhered to the surface thereof. The distal reinforcing band 70 may provide tear resistance in the vicinity of sutures or other attachment devices associated with elements or aspects of the heart valve implant. For example, in some embodiments, a plurality of valve leaflets may be secured to the distal reinforcing band 70.

In some embodiments, the distal reinforcing band 70 also may include a plurality of perforations, the plurality of perforations extending through both the distal reinforcing band 70 and the seal member 50. In some embodiments, the plurality of perforations may accommodate sutures passing therethrough to secure elements or aspects of the heart valve implant, such as (but not limited to) a plurality of valve leaflets, for example. In the some embodiments, the distal reinforcing band 70 may comprise a woven fabric or a nonwoven fabric, such as a polyester fiber fabric or other suitable material.

Although in the example(s) above three layers of polymeric material was employed, it will be appreciated that a greater or lesser number of layers may be employed and that each of the three or more layers may comprise two or more sublayers. Additionally, the distal reinforcing band 70 could be positioned at multiple locations within the seal member 50 including within a layer, or on the radially innermost or radially outermost surface of the seal member 50. As noted herein, in some embodiments, more than a single distal reinforcing band 70 may be incorporated, for example a first band may be positioned between a first and second layer of the seal member 50 and a second band may be positioned between a second and third layer of the seal member 50. It will also be appreciated that it is not necessary that each distal reinforcing band 70 be located at the same axial position along the seal member 50 and/or within the seal member 50.

In some embodiments, during fabrication of the support structure 10, the distal reinforcing band 70 may be positioned on the mandrel 100, for example by inserting locating pins in apertures in the mandrel 100 which may align with corresponding perforations provided in the distal reinforcing band 70. In some instances, it may be desirable to secure the distal reinforcing band 70 to the mandrel 100 or to the seal member 50 by applying a drop of a polymeric material or polymer solution, or other adhesive composition, to each item to ensure that it remains properly positioned during subsequent processing. In some embodiments, the distal reinforcing band 70 may be positioned on the mandrel 100 before the expandable scaffold 20, after the expandable scaffold 20 and before the polymeric material and/or seal member 50, between layers of the seal member 50, or after the seal member 50 has been completed. In general, the distal reinforcing band 70 may be positioned on the mandrel and/or the support structure 10 before curing the polymeric material and/or the seal member 50.

In some embodiments, after curing the polymeric material (i.e., the first layer, the second layer, and/or the third layer, etc.) and/or the seal member 50, the temporary masking 30 may be dissolved and/or removed off of the at least one section of the seal portion 22 or the expandable scaffold 20, and the masking 130 may be removed and/or dissolved off of the mandrel 100. In at least some embodiments, the temporary masking 30 and/or the masking 130 may be water soluble. In some embodiments, the mandrel 100, with the support structure 10 positioned thereon, may be dipped into a water bath 400 to dissolve the temporary masking 30 and/or the masking 130. In some embodiments, the mandrel 100, with the support structure 10 positioned thereon, may be rinsed with a shower-like apparatus, or other suitable rinsing apparatus. In some embodiments, the temporary masking 30 and/or the masking 130 may not be water soluble. In such embodiments, other suitable rinsing and/or dissolving agents may be used to remove the temporary masking 30 and/or the masking 130 as appropriate.

Figure 13:
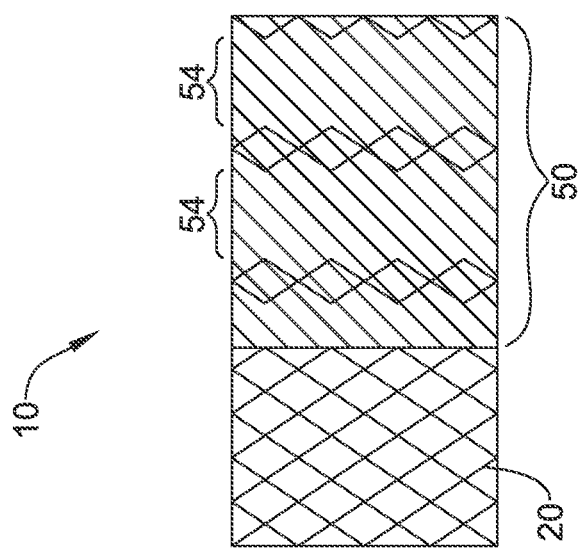

After dissolving the temporary masking 30 and/or the masking 130, the seal member 50 may be trimmed, for example by laser cutting or other suitable means, to conform to dimensional specifications, and the support structure 10 removed from the mandrel 100. In some embodiments, the support structure 10 may be removed from the mandrel 100 before trimming the seal member 50. A support structure 10 having an untrimmed seal member 50 may be seen illustratively in FIG. 13, while a support structure 10 having a trimmed seal member 50 may be seen illustratively in FIG. 14. FIG. 14A illustrates a partial sectional view of the trimmed seal member 50 after dissolving the temporary masking 30. In some embodiments, at least some of the perforations in the distal reinforcing band 70 may be formed by laser cutting.

Figure 15:
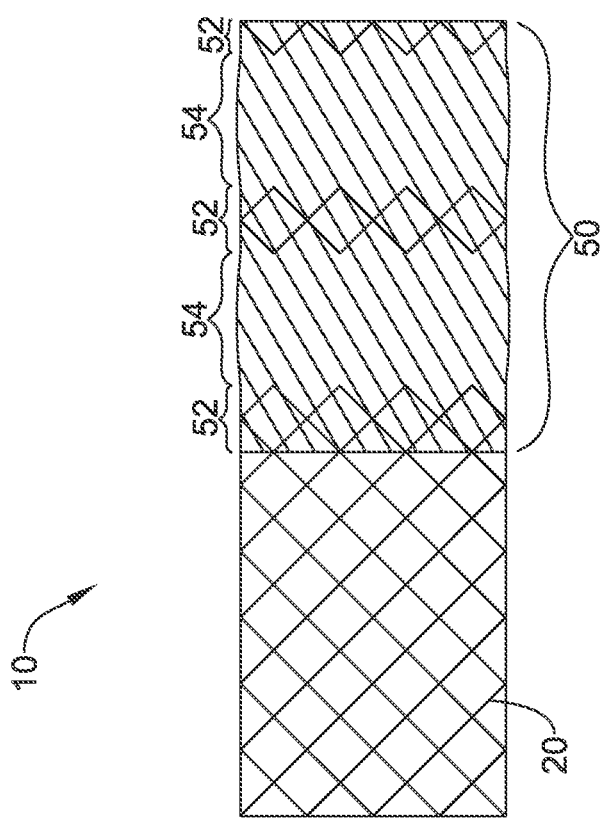
FIG. 15 illustrates an example support structure in a delivery configuration.
Figure 16:
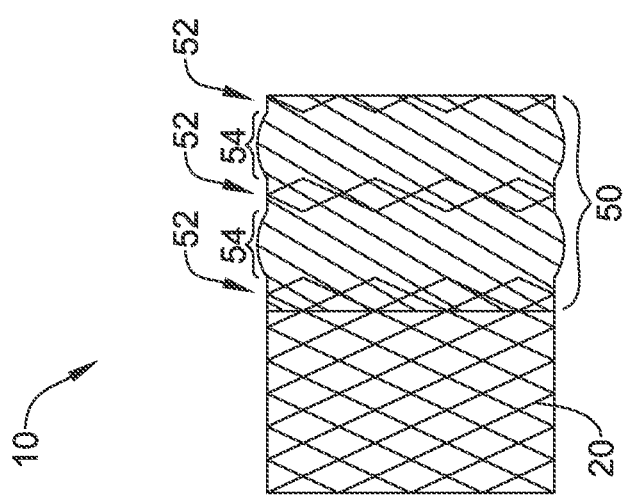
FIG. 16 illustrates an example support structure in a deployed configuration.

FIG. 15 illustrates a support structure 10 having an expandable scaffold 20 in a delivery configuration. As may be seen in FIG. 15, when the expandable scaffold is in the delivery configuration, the second portion 54 of the seal member 50 lies generally flush against an outer surface of the expandable scaffold 20. Such an arrangement provides for ease of sheathing and delivery of the support structure 10 to a treatment site. FIG. 16 illustrates a support structure 10 having an expandable scaffold 20 in a deployed configuration. As may be seen in FIG. 16, when the expandable scaffold 20 is in the deployed configuration, the second portion 54 of the seal member 50 bulges radially outward from the expandable scaffold 20. The bulging seal member 50 may serve to seal the support structure 10 against the tissue(s) of the treatment site to minimize or prevent paravalvular regurgitation or leakage around an outer perimeter of the support structure 10 and/or a heart valve implant associated therewith.

Although generally described above, a method of making a support structure 10 for a heart valve implant may comprise positioning an expandable scaffold (e.g., an expandable metallic scaffold) on a mandrel 100 in a coating apparatus, the expandable scaffold having a seal portion 22 configured to receive a polymeric material thereon. In some embodiments, a method of making a support structure 10 may include applying a masking 130 to the mandrel 100 prior to positioning the expandable scaffold 20 thereon. In some embodiments, a method of making a support structure 10 may include applying a temporary masking 30 to at least one section of the seal portion 22 of the expandable scaffold 20. In some embodiments, a method of making a support structure 10 may include applying a first layer of the polymeric material onto the seal portion 22 of the scaffold to form a seal member 50. In some embodiments, a method of making a support structure 10 may include curing the first layer of the polymeric material. In some embodiments, a method of making a support structure 10 may include applying a second layer of the polymeric material onto the seal portion 22 and/or the first layer. In some embodiments, a method of making a support structure 10 may include curing the second layer of the polymeric material. In some embodiments, a method of making a support structure 10 may include dissolving the temporary masking 30 off of the seal portion 22 of the expandable scaffold 20. In some embodiments, a method of making a support structure 10 may include dissolving the masking 130 off of the mandrel 100 to release the support structure 10 therefrom. In some embodiments, a method of making a support structure 10 may include removing the expandable scaffold 20 from the mandrel 100. In some embodiments, a method of making a support structure 10 may include trimming the seal member 50 using a laser.

In some embodiments, a method of making a support structure 10 may include applying a third layer of polymeric material onto the seal portion 22 and/or the second layer. In some embodiments, a method of making a support structure 10 may include curing the third later of the polymeric material. In some embodiments, a method of making a support structure 10 may include, before applying the third layer, a distal reinforcing band 70 positioned around the expandable scaffold 20 at a distal end thereof. In some embodiments, applying the third layer may at least partially embed the distal reinforcing band 70 within the polymeric material.

In some embodiments, a method of making a support structure 10 may include the temporary masking 30 being water soluble. In some embodiments, dissolving the temporary masking 30 may include applying water to the support structure 10 and/or the expandable scaffold 20. In some embodiments, a method of making a support structure 10 may include the masking 130 being water soluble. In some embodiments, dissolving the masking 130 may include applying water to the mandrel 100 and/or the support structure 10. In some embodiments, a method of making a support structure 10 may include the seal member 50 being unattached to the expandable scaffold 20 at the at least one section of the seal portion 22 after dissolving the temporary masking 30. In some embodiments, a method of making a support structure 10 may include adding one or more reinforcing members 60 to the polymeric material prior to curing. In some embodiments, applying the layers of polymeric material may include spraying the polymeric material onto the seal portion 22. In some embodiments, applying the layers of polymeric material may include dipping the seal portion 22 of the expandable scaffold 20 into the polymeric material. Other steps and/or methods are also contemplated.

Although the illustrative examples described above relate to a support structure for a heart valve implant, similar support structures may be fabricated and attached to a variety of other implantable devices such as, for example, stents and aneurysm plugs. In such embodiments, the mandrel may have a different geometry and different polymers may be selected for the seal member and/or layers of the seal member.

It should be understood that although the above discussion was focused on a medical device for use within the vascular system and/or the heart of a patient, other embodiments of medical devices or methods in accordance with the disclosure can be adapted and configured for use in other parts of the anatomy of a patient. For example, devices and methods in accordance with the disclosure can be adapted for use in the digestive or gastrointestinal tract, such as in the mouth, throat, small and large intestine, colon, rectum, and the like. For another example, devices and methods can be adapted and configured for use within the respiratory tract, such as in the mouth, nose, throat, bronchial passages, nasal passages, lungs, and the like. Similarly, the apparatus and/or medical devices described herein with respect to percutaneous deployment may be used in other types of surgical procedures as appropriate. For example, in some embodiments, the medical devices may be deployed in a non-percutaneous procedure, such as an open heart procedure. Devices and methods in accordance with the invention can also be adapted and configured for other uses within the anatomy.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims. This may include, to the extent that it is appropriate, the use of any of the features of one example embodiment or aspect being used in other embodiments or aspects.

What is claimed is:

1. A method of making a support structure for a heart valve implant, comprising:
    positioning an expandable metallic scaffold on a mandrel in a coating apparatus, the scaffold having a seal portion configured to receive a polymeric material thereon;
    applying a masking to at least one section of the seal portion of the expandable scaffold;
    applying a first layer of the polymeric material onto the seal portion of the expandable scaffold to form a seal member, wherein each of the at least one section of the seal portion having the masking is disposed between adjacent sections of the seal portion devoid of the masking;
    curing the first layer;
    applying a second layer of the polymeric material onto the first layer;
    curing the second layer;
    dissolving the masking off of the at least one section of the seal portion of the expandable scaffold, wherein after dissolving the masking, the seal member is unattached to the expandable scaffold at the at least one section of the seal portion and the seal member is attached to the expandable scaffold at the adjacent sections of the seal portion; and
    removing the expandable scaffold from the mandrel.

2. The method of claim 1, further comprising:
    applying a third layer of the polymeric material onto the second layer; and
    curing the third layer.

3. The method of claim 2, wherein before applying the third layer, a reinforcing band is positioned around the expandable scaffold at a distal end thereof;
    wherein applying the third layer at least partially embeds the reinforcing band within the polymeric material.

4. The method of claim 1, wherein the masking is water soluble.

5. The method of claim 4, wherein dissolving the masking includes applying water to the expandable scaffold.

6. The method of claim 1, further including:
    adding one or more reinforcing members to the polymeric material prior to curing.

7. The method of claim 1, wherein applying the layers of polymeric material includes spraying the polymeric material.

8. The method of claim 1, wherein applying the layers of polymeric material include dipping the seal portion of the expandable scaffold into the polymeric material.

* * * * *